US00PP35335P2

(12) United States Plant Patent
Danziger

(10) Patent No.: US PP35,335 P2
(45) Date of Patent: Aug. 22, 2023

(54) ***VERBENA* PLANT NAMED 'DVERVACMRS'**

(50) Latin Name: *Verbena hortensis*
Varietal Denomination: DVERVACMRS

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 18/087,524

(22) Filed: Dec. 22, 2022

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Verbena* plant named 'DVERVACMRS' is disclosed, characterized by abundant pink flowers with vivid, darker pink centers. Plants have compact, mounded habits, and are tolerant to powdery mildew. The new variety is a *Verbena*, typically produced as an ornamental plant.

2 Drawing Sheets

Latin name of the genus and species: *Verbena hortensis*.
Variety denomination: 'DVERVACMRS'.

BACKGROUND OF THE INVENTION

The new *Verbena* cultivar is a product of a planned breeding program conducted by the inventor, Gavriel Danziger in Moshav Mishmar Hashiva, Israel. The objective of the breeding program was to produce new *Verbena* varieties for ornamental horticultural production. The open-pollination resulting in this new variety was made during October of 2018.

The seed parent is the unpatented, propriety variety referred to as *Verbena* 'VE-15-8019'. The pollen parent is unknown. The new variety was discovered in April of 2019 by the inventor in a group of seedlings resulting from the 2018 open-pollination, in a greenhouse in Moshav Mishmar Hashiva, Israel. After selection of the new variety, extensive confidential testing has been performed to determine and define the desirable characteristics of the new variety.

Asexual propagation of *Verbena* was performed by vegetative cuttings in April of 2019, at the same nursery in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DVERVACMRS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERVACMRS'. These characteristics in combination distinguish 'DVERVACMRS' as a new and distinct *Verbena* cultivar:

1. Early, abundant flowering.
2. Compact, mounded habit.

3. Tolerant to powdery mildew.
4. Pink flowers with vivid, darker pink centers.

PARENT COMPARISON

Plants of 'DVERVACMRS' are similar in some horticultural characteristics to the seed parent. The new variety, however, differs in the following:

1. Flowers of the new variety have a darker pink center than flowers of the seed parent.
2. Internodes of the new variety are shorter than internodes of the seed parent.
3. The new variety is tolerant to powdery mildew, while the seed parent is not.

COMMERCIAL COMPARISONS

Plants of 'DVERVACMRS' are similar in some horticultural characteristics to the variety *Verbena* 'DVERDEPINK', U.S. Plant Pat. No. 29,014. The new variety, however, differs in the following:

1. Flowers of the new variety have a darker pink center than flowers of this comparator.

Plants of 'DVERVACMRS' are similar in some horticultural characteristics to the variety *Verbena* 'Balendpibi', U.S. Plant Pat. No. 28,455. The new variety, however, differs in the following:

1. Plants of the new variety are more compact than plants of this comparator.

BRIEF DESCRIPTION OF THE PHOTOGRAPHS

Figure 1:
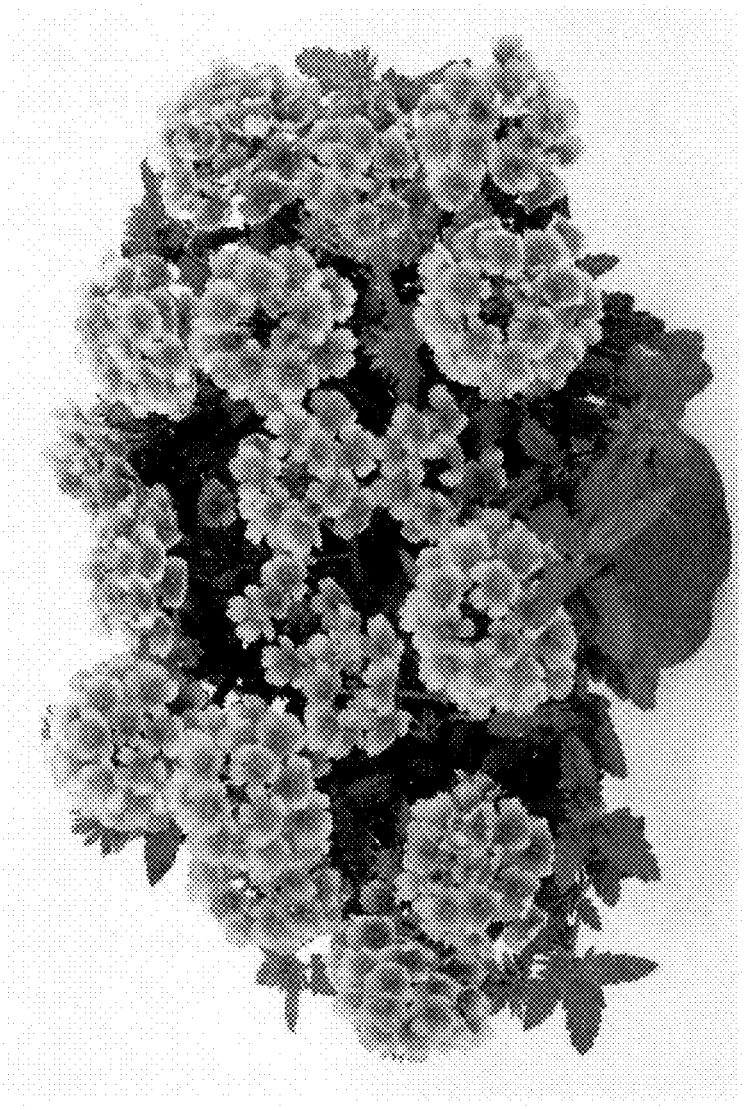

The accompanying photograph in FIG. 1 illustrates in full color a typical plant of 'DVERVACMRS' at about 3 months of age, grown in a 12 cm pot.

Figure 2:
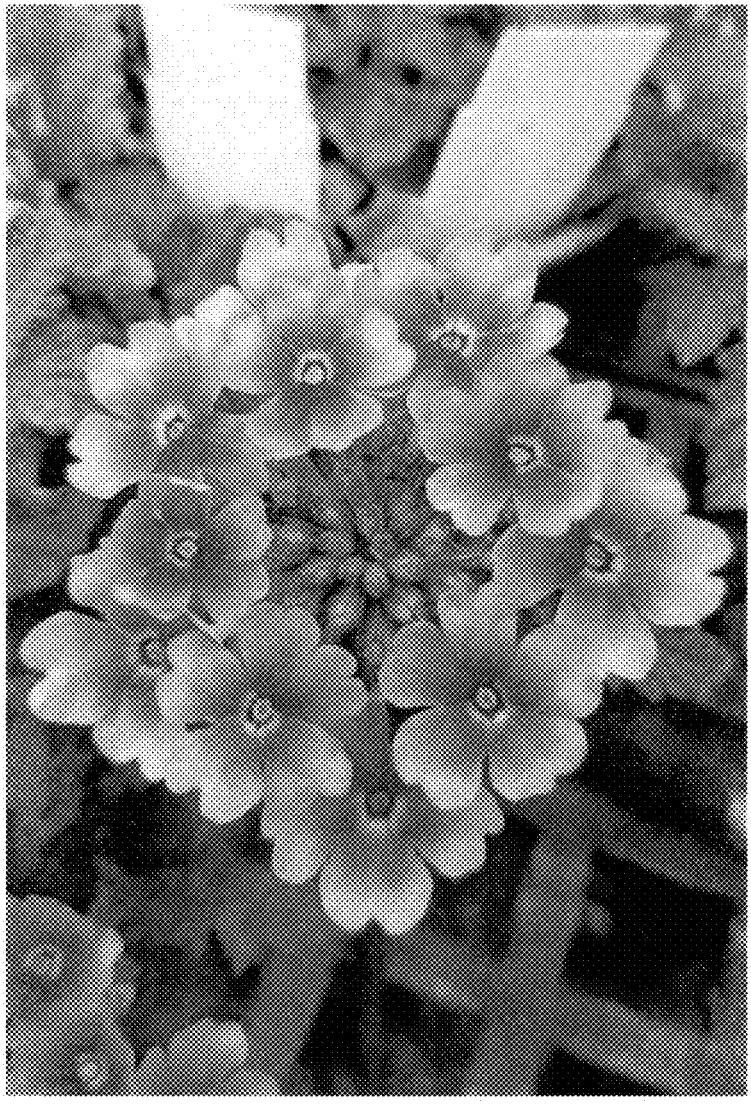

FIG. 2 illustrates a close-up view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVERVACMRS' plants grown in a greenhouse in Moshav Mishmar Hashiva, Israel, under natural lighting. Measurements were taken during autumn. The growing temperature ranged from approximately 18° C. to 27° C. during the days, 10° C. to 15° C. during the nights. Measurements and numerical values represent averages of typical plant types.

Botanical classification: *Verbena hortensis* 'DVERVACMRS'.

PROPAGATION

Time to initiate rooting: 7 to 9 days at approximately 23° C.
Age of plant described: 90 days from a rooted cutting.

PLANT

Growth habit: Compact, mounded.
Pot size of plant described: 12 cm.
Height: 20 cm.
Plant spread: 30 cm.
Growth rate: Rapid.
Branching characteristics: Freely branching.
Length of lateral branches: 15 cm.
Diameter of lateral branches: 0.35 cm.
Quantity of lateral branches: 10.
Characteristics of lateral branches:
- *Shape*.—Cylindrical.
- *Texture*.—Pubescent.
- *Strength*.—Flexible.
- *Color*.—RHS Yellow-Green 144A.

Internode length: 3 cm.

FOLIAGE

Leaf:
- *Arrangement*.—Opposite.
- *Quantity*.—Approximately 16 per branch.
- *Average length*.—3.5 cm.
- *Average width*.—2 cm.
- *Pubescence*.—Strigose.
- *Shape*.—Triangular.
- *Apex*.—Acute.
- *Base*.—Acute.
- *Margin*.—Serrate.
- *Texture*.—Pubescent.
- *Aspect*.—45°.
- *Color*.—Young Foliage, Upper Side: RHS Green 137B. Young Foliage, Under Side: RHS Green 138B. Mature Foliage, Upper Side: RHS Green 137A. Mature Foliage, Under Side: RHS Green 138B.
- *Venation*.—Type: Cross venulate. Color, Upper Side: RHS Yellow-Green 144B. Color, Under Side: RHS Yellow-Green 145B.

Petiole:
- *Length*.—0.7 cm.
- *Diameter*.—0.2 cm.
- *Color*.—RHS Yellow-Green 144B.
- *Texture*.—Pubescent.

FLOWER

Natural flowering season: Spring to autumn.
Days to flowering from rooted cutting: 21 to 28 days.
Inflorescence and flower type and habit: Terminal cluster.
Rate of flower opening: 4 to 6 days from bud to fully opened flower.
Flower longevity on plant: 5 to 8 days.
Persistent or self-cleaning: Self-cleaning.
Bud:
- *Shape*.—Quinquangular.
- *Length*.—0.8 cm.
- *Diameter*.—0.2 cm.
- *Color*.—RHS Green 142A.

Corolla:
- *Flower*.—Diameter: 2 cm. Depth: 1.5 cm.
- *Petals/lobes*.—Length: 1 cm. Width: 0.7 cm. Quantity: 5. Texture: Smooth. Aspect. Upright. Shape: Obcordate. Apex: Rounded. Margin: Entire. Color: When Opening: Upper Surface Primary Color: RHS Red-Purple 73A. Lower Surface Primary Color: RHS Red-Purple 74B. Upper Surface Secondary Color (center eye): RHS Red-Purple 71B. Fully Opened: Upper Surface Primary Color: RHS Red-Purple 72D. Lower Surface Primary Color: RHS Red-Purple 75A. Upper Surface Secondary Color (center eye): RHS Red-Purple 71B.
- *Throat*.—Color: RHS Yellow-Green 149D. Tube Color: RHS Yellow-Green 149D.
- *Calyx*.—Form: Tubular. Length: 1.2 cm. Diameter: 0.2 cm. Sepal Shape: 5 sepals whose margins are fused — quinquangular. Sepal Margin: Entire. Sepal Color: RHS Yellow-Green 143C, upper and lower surfaces. Sepal Texture: Coarsely pubescent.

Fragrance: None.

REPRODUCTIVE ORGANS

Androecium:
Stamens:
- *Quantity*.—4.
- *Filament length*.—0.1 cm.

Anthers:
- *Shape*.—Conical.
- *Length*.—About 0.1 cm.
- *Color*.—RHS Yellow-Green 150B.
- *Pollen*.—Color: RHS Yellow-Green 150B. Amount: Moderate.

Gynoecium:
Pistil:
- *Quantity*.—1.
- *Length*.—2 cm.
- *Style*.—Length: 0.1 cm. Color: RHS Yellow-Green 144C.
- *Stigma*.—Shape: Ovoid. Color: RHS Yellow-Green 144B.

OTHER CHARACTERISTICS

Seeds and fruits: None observed.
Disease/pest resistance: Tolerant to powdery mildew.
Temperature tolerance: Tolerant from −1° C. to 32° C.

What is claimed is:

1. A new and distinct cultivar of *Verbena* plant named 'DVERVACMRS' as herein illustrated and described.

* * * * *